US00PP37508P2

(12) United States Plant Patent
Schoone

(10) Patent No.: US PP37,508 P2
(45) Date of Patent: Jun. 30, 2026

(54) ***PHALAENOPSIS* PLANT NAMED 'Helix Bridge'**

(50) Latin Name: *Phalaenopsis hybrida*
Varietal Denomination: Helix Bridge

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/354,774

(22) Filed: Oct. 9, 2025

Related U.S. Application Data

(60) Provisional application No. 63/714,593, filed on Oct. 31, 2024.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

(56) References Cited

PUBLICATIONS

U.S. Appl. No. 19/243,678 Allowance issued Oct. 23, 2025 patent number not yet assigned. effective filing date Jun. 20, 2024. (Year: 2024).*

* cited by examiner

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'Helix Bridge', characterized by its upright plant habit; moderately vigorous growth habit; strong flowering stems; healthy and sturdy leaves; freely flowering habit with typically two inflorescences developing per plant, each inflorescence with numerous flowers; flower petals and sepals that are reddish purple in color; and good postproduction longevity.

2 Drawing Sheets

Figure 1:
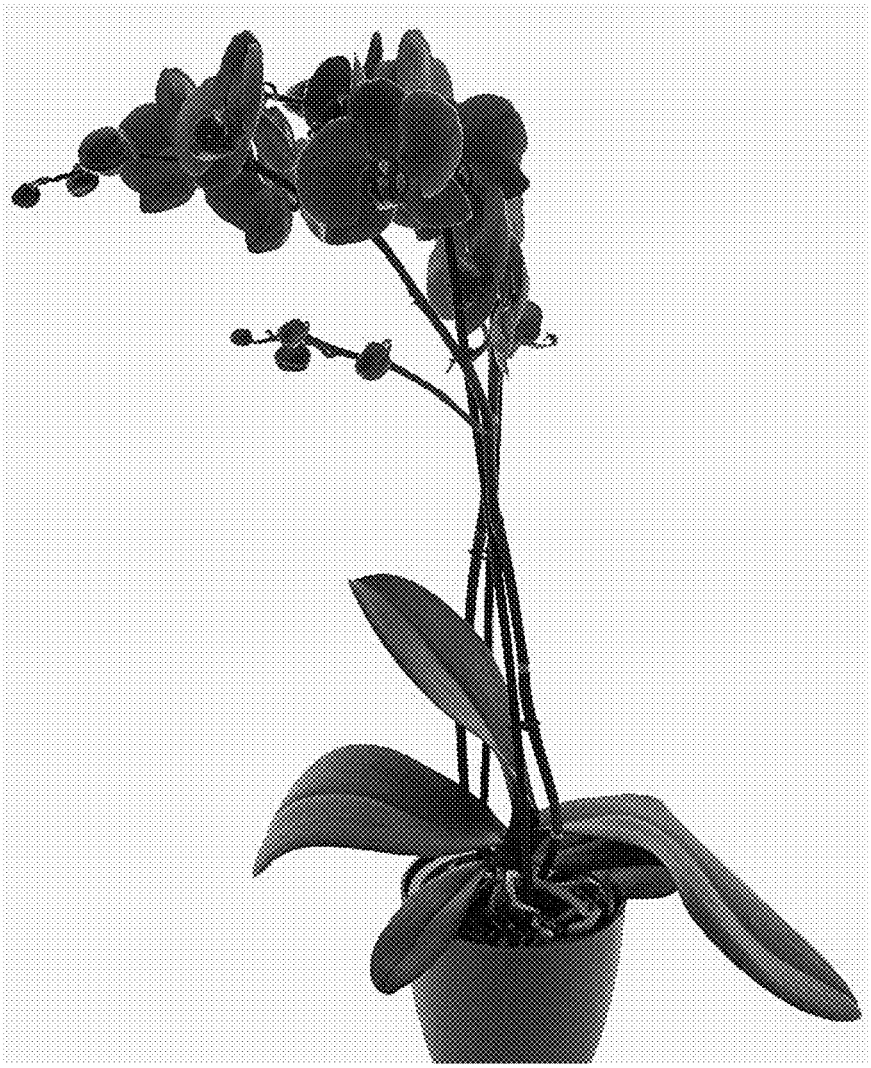

Botanical designation: *Phalaenopsis hybrida.*
Cultivar denomination: 'HELIX BRIDGE'.

CROSS-REFERENCED TO CLOSELY-RELATED APPLICATIONS

A European Community Plant Breeder's Rights application for the instant plant was filed by the Applicant/Assignee, Floricultura B.V. of Heemskerk, The Netherlands on Oct. 9, 2024, application number 2024/2358. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Helix Bridge'.

The new *Phalaenopsis* plant is a product of a planned breeding program conducted by the Inventor in De Lier, Heemskerk and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in August, 2014 in De Lier, The Netherlands of a proprietary selection of *Phalaenopsis hybrida* identified as code number 362644, not patented, as the female, or seed, parent with a proprietary selection of *Phalaenopsis hybrida* identified as code number B3024, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November, 2020.

Asexual reproduction of the new *Phalaenopsis* plant by in vitro meristem propagation in a controlled environment in Assendelft, The Netherlands since December, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Helix Bridge'. These characteristics in combination distinguish 'Helix Bridge' as a new and distinct *Phalaenopsis* plant:

1. Upright plant habit.
2. Moderately vigorous growth habit.
3. Strong flowering stems.

4. Healthy and sturdy leaves.
5. Freely flowering habit with typically two inflorescences developing per plant, each inflorescence with numerous flowers.
6. Flower petals and sepals that are reddish purple in color.
7. Good postproduction longevity.

Plants of the new *Phalaenopsis* can be compared to plants of the female parent selection. Plants of the new *Phalaenopsis* differ primarily from plants of the female parent selection in the following characteristics:

1. At the base of the flower petals of plants of the new *Phalaenopsis* there are fine dots whereas at the base of the flower petals of plants of the female parent selection there are no dots.
2. Cirrhose apices of the labella of plants of the new *Phalaenopsis* are lighter in color than cirrhose apices of the labella of plants of the female parent selection.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* are not netted whereas flower petals of plants of the male parent selection are netted.
2. Cirrhose apices of the labella of plants of the new *Phalaenopsis* are lighter in color than cirrhose apices of the labella of plants of the male parent selection.

Plants of the new *Phalaenopsis* can be compared to plants of x *Phalaenopsis hybrida* 'Coronado', disclosed in U.S. Plant patent application Ser. No. 19/243,678. In side-by-side comparisons, plants of the new *Phalaenopsis* differ primarily from plants of 'Coronado' in the following characteristics:

1. Flowers of plants of the new *Phalaenopsis* are broader than flowers of plants of 'Coronado'.
2. Flower petals of plants of the new *Phalaenopsis* are not netted whereas flower petals of plants of 'Coronado' are netted.
3. Flower columns of plants of the new *Phalaenopsis* are mostly reddish purple in color whereas flower columns of plants of 'Coronado' are mostly dark yellow in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Helix Bridge' grown in a container.

Figure 2:
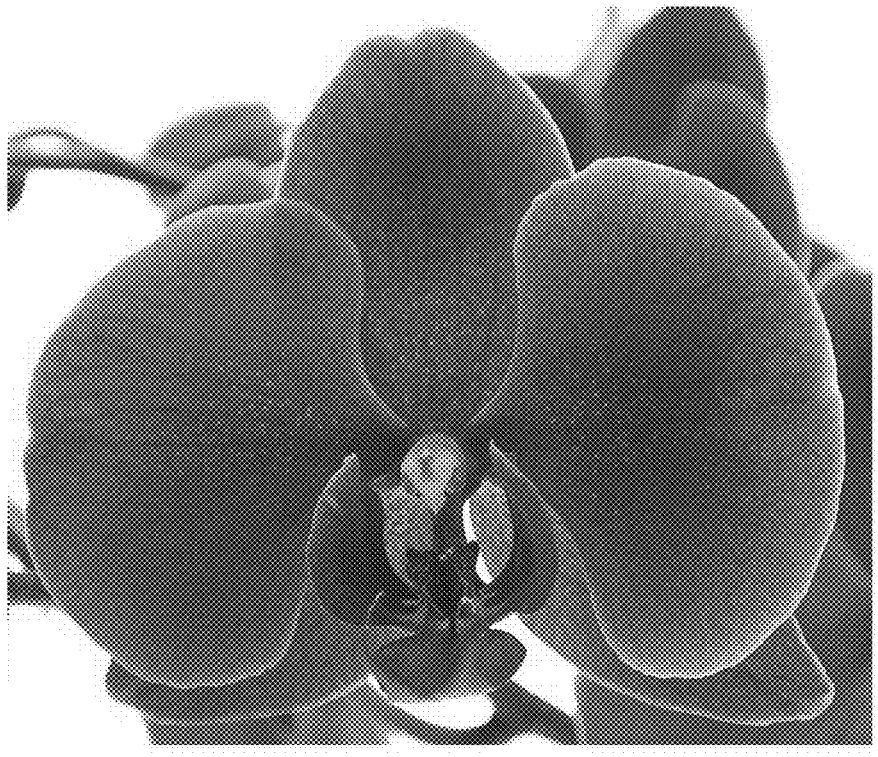

The photograph on the second sheet (FIG. 2) is a close-up view of a typical flower of 'Helix Bridge'.

DETAILED BOTANICAL DESCRIPTION

The aforementioned photographs and following observations and measurements describe plants grown during the winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Helix Bridge'.

Parentage:

*Female, or seed, parent*.—Proprietary selection of *Phalaenopsis hybrida* identified as code number 362644, not patented.

*Male, or pollen, parent*.—Proprietary selection of *Phalaenopsis hybrida* identified as code number B3024, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous and moderate growth rate.

*Plant height, substrate level to top of foliar plane*.—About 16 cm.

*Plant height, substrate level to top of floral plane*.—About 48.7 cm.

*Plant diameter or spread*.—About 30.1 cm.

Leaf description:

*Arrangement and quantity*.—Distichous, simple; sessile; about four to five fully-developed leaves per plant.

*Length*.—About 21.5 cm.

*Width*.—About 8.3 cm.

*Aspect*.—Semi-drooping to drooping.

*Shape*.—Elliptic to elliptic-oblong; slightly carinate.

*Apex*.—Unequal broadly acute.

*Base*.—Sheathing. Sheath length: About 2.3 cm. Sheath width: About 1.7 cm. Sheath color, upper and lower surfaces: Close to 147B, slightly to strongly tinged with close to N186C.

*Margin*.—Entire.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to a blend of NN137B and 147A; narrow marginal edges, close to a blend of N186C and 200B. Developing leaves, lower surface: Close to 147A strongly tinged with close to 200A; narrow marginal edges, close to a blend of N186C and 200B. Fully expanded leaves, upper surface: Close to NN137A; narrow marginal edges, close to N200A; venation, close to 147A. Fully expanded leaves, lower surface: Close to 146A; narrow marginal edges, close to N200A slightly to strongly tinged with close to 200A and N186C; venation, close to 200A tinged with close to N186C.

Inflorescence description:

Appearance and flowering habit.—Showy zygomorphic flowers arranged on axillary simple or branched racemes; typically two inflorescences develop per plant; each inflorescence with about 13 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 27.6 cm.

*Inflorescence width*.—About 17 cm.

*Flower buds* (*about one week before flower opening*).—Height: About 1.9 cm. Diameter: About 1.5 cm. Shape: Broadly ovoid. Color: Close to a blend of N79B and N79C; venation, close to N79B.

*Flower size*.—About 7.8 cm (vertical) by 9 cm (horizontal).

*Flower depth*.—About 3 cm.

*Petals, quantity and arrangement*.—Three, two lateral petals and one center petal transformed into a labellum.

*Lateral petals*.—Length: About 4.2 cm. Width: About 5.6 cm. Shape: Broadly reniform; not imbricate. Apex: Shallow retuse. Margin: Entire. Texture and luster, upper surface: Smooth, glabrous; velvety; matte. Texture and luster, lower surface: Smooth, glabrous; moderately velvety; matte. Color: When opening, upper surface: Close to NN78A; narrow marginal edges, close to 76C. When opening, lower surface: Close to N78A; narrow marginal edges, close to 76C. Fully opened, upper surface: Close to NN78A; narrow marginal edges, close to 76C; at the base, fine dots, close to 76B; venation, close to NN78A; colors do not change with subsequent development. Fully opened, lower surface: Close to N78B; narrow marginal edges, close to 76C; colors do not change with subsequent development.

*Labella*.—Appearance: Three-parted with two lateral lobes and a central lobe. Length, lateral lobes: About 2.1 cm. Width, lateral lobes: About 1.7 cm. Length, central lobe: About 2.2 cm. Width, central lobe: About 0.9 cm to 1.7 cm. Length, cirrhose apices: About 1.2 cm. Shape, lateral lobes: Broadly obovate. Shape, central lobe: Ovate-oblong. Apex, lateral lobes: Obtuse. Apex, central lobe: Cleft with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 7 mm in width and about 6 mm in height. Color, lateral lobes: When opening, upper surface: Close to 187C; towards the apex, close to 72A. When opening, lower surface: Close to N78A; towards the base, close to 71A with basal margin, close to 158A. Fully opened, upper surface: Close to 187C; towards the apex, close to 72A. Fully opened, lower surface Close to N78B; central blotch, close to 76A; towards the base, close to 71A and 71B with basal margin, close to 158A. Color, central lobe: When opening and fully opened, upper surface: Close to 71B; towards the base, close to 71A; at the base, close to 187C and 71B; cirrhose apices, close to N79C and distally, close to N79B with serrations, close to 156D. When opening and fully opened, lower surface: Close to N78B; towards the apex and margins, close to N79C; at the base, close to 156B and N79C; cirrhose apices, close to N79C and distally, close to N79B with serrations, close to 156D. Color, callosities: When developing: Close to N34C; laterally, close to 22A. Fully developed: Close to 39A with fine stripes, close to 22A; laterally, close to N34C.

*Sepals*.—Quantity and arrangement: Three, one upper dorsal sepal and two lower lateral sepals. Length, dorsal sepal: About 4.4 cm. Width, dorsal sepal: About 3.4 cm. Length, lateral sepals: About 4.4 cm. Width, lateral sepals: About 3 cm. Shape, dorsal sepal: Broadly elliptic-oblong. Shape, lateral sepals: Ovate. Apex, dorsal sepal: Retuse to emarginate. Apex, lateral sepals: Bluntly acute. Base, dorsal and lateral sepals: Cuneate. Margins, dorsal and lateral sepals: Entire. Texture and luster, dorsal and lateral sepals, upper surface: Smooth, glabrous; velvety; matte. Texture and luster, dorsal and lateral sepals, lower surface: Smooth, glabrous; slightly velvety; moderately glossy. Color, dorsal sepal: When opening, upper surface: Close to a blend of NN78A and N79C; towards the apex and margins, close to NN78A; fine dots, close to 76B; venation, close to N79C. When opening, lower surface: Close to N79C; towards the base and margins, close to N78A; venation, close to N79C. Fully opened, upper surface: Close to a blend of NN78A and N79C; towards the apex and margins, close to NN78B; fine dots, close to 76B; venation, close to N79C. Fully opened, lower surface: Close to a blend of 71A and N79C; towards the apex, base and margins, close to N78B; venation, close to N79C. Color, lateral sepals: When opening, upper surface: Upper half, close to NN78A; lower half, close to a blend of N79C and N79D; towards the base, fine dots, close to 156A; venation, close to N79C. When opening, lower surface: Close to N79C; towards the margins, close to N78A; towards the base, close to N78A tinged with close to 185C; venation, close to N79C. Fully opened, upper surface: Upper half, close to NN78A; lower half, close to 71A; towards the base, fine dots, close to 156A; venation, close to N79C. Fully opened, lower surface: Close to a blend of 71A and N79C; towards the apex and margins, close to N78B; towards the base, close to N78B tinged with close to 185D; venation, close to N79C.

*Peduncles*.—Length: About 54.5 cm. Diameter: About 5.5 mm. Strength: Strong. Aspect: Upright to outwardly arching. Texture and luster: Smooth, glabrous; matte. Color: Close to a blend of N186A and 200A; densely covered with fine dots and fine marbling, close to 147C and 147D.

*Pedicels*.—Length: About 3.6 cm. Diameter: About 4 mm. Strength: Moderately strong. Aspect: About 70° from peduncle axis. Texture and luster: Smooth, glabrous; matte. Color: Close to N77B; distal end, close to N155C; proximal end, close to N186C.

*Reproductive organs*.—Androecium: Column length: About 8 mm. Column width: About 6 mm. Column color: Close to NN78C; at the apex, tinged with close to N155A. Pollinia quantity: Two. Pollinia diameter (per two pollinia): About 2.5 mm. Pollinia color: Close to 23A. Gynoecium: Stigma length: About 4 mm. Stigma width: About 4.5 mm. Stigma shape: Reniform. Stigma color: Close to 76D. Ovary length: About 1 cm. Ovary diameter: About 1 mm. Ovary color: Close to 150D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Helix Bridge' as herein illustrated and described.

* * * * *